(12) United States Patent
Baranson et al.

(10) Patent No.: US 12,099,178 B2
(45) Date of Patent: Sep. 24, 2024

(54) KINEMATIC IMAGING SYSTEM

(71) Applicant: Singular Genomics Systems, Inc., La Jolla, CA (US)

(72) Inventors: David Baranson, Encinitas, CA (US); Eli N. Glezer, Del Mar, CA (US); David L. Heiner, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 210 days.

(21) Appl. No.: 17/552,759

(22) Filed: Dec. 16, 2021

(65) Prior Publication Data

US 2022/0187587 A1 Jun. 16, 2022

Related U.S. Application Data

(60) Provisional application No. 63/126,103, filed on Dec. 16, 2020.

(51) Int. Cl.
*G02B 21/36* (2006.01)
*G01N 21/64* (2006.01)
*G02B 21/16* (2006.01)
*H04N 23/67* (2023.01)
*H04N 23/695* (2023.01)

(52) U.S. Cl.
CPC ....... *G02B 21/362* (2013.01); *G01N 21/6428* (2013.01); *G01N 21/6458* (2013.01); *G02B 21/16* (2013.01); *H04N 23/67* (2023.01); *H04N 23/695* (2023.01); *G01N 2021/6439* (2013.01)

(58) Field of Classification Search
CPC .. G02B 21/362; G02B 21/16; G01N 21/6428; G01N 21/6458; G01N 2021/6439; H04N 23/67; H04N 23/695
See application file for complete search history.

(56) References Cited

U.S. PATENT DOCUMENTS

| | | |
|---|---|---|
| 7,057,026 B2 | 6/2006 | Barnes et al. |
| 7,541,444 B2 | 6/2009 | Milton et al. |
| 8,039,817 B2 | 10/2011 | Feng et al. |
| 8,241,573 B2 | 8/2012 | Banerjee et al. |
| 10,738,072 B1 | 8/2020 | Graham et al. |
| 2006/0250518 A1 | 11/2006 | Nilson et al. |
| 2007/0114362 A1 | 5/2007 | Feng et al. |
| 2009/0026082 A1 | 1/2009 | Rothberg et al. |
| 2009/0250615 A1 | 10/2009 | Oldham et al. |
| 2011/0128552 A1 | 6/2011 | Hadcock et al. |
| 2011/0304722 A1 | 12/2011 | Nilsson et al. |

(Continued)

FOREIGN PATENT DOCUMENTS

| | | |
|---|---|---|
| WO | WO-2004/018497 A2 | 3/2004 |
| WO | WO-2004/018497 A3 | 3/2004 |

(Continued)

OTHER PUBLICATIONS

Bentley, D.R. et al. (Nov. 6, 2008). "Accurate whole human genome sequencing using reversible terminator chemistry," *Nature* 456(7218):53-59.

(Continued)

*Primary Examiner* — Christopher K Peterson
(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are imaging systems, devices, and methods of use thereof.

19 Claims, 5 Drawing Sheets

(56) References Cited

U.S. PATENT DOCUMENTS

| | | | |
|---|---|---|---|
| 2012/0270305 A1 | 10/2012 | Reed et al. | |
| 2014/0267669 A1 | 9/2014 | Stoops et al. | |
| 2016/0199138 A1* | 7/2016 | Cooper | A61B 34/70 606/130 |
| 2018/0097999 A1* | 4/2018 | Kim | G01N 21/84 |
| 2019/0137752 A1* | 5/2019 | Shaffer | G02B 21/0012 |

FOREIGN PATENT DOCUMENTS

| | | |
|---|---|---|
| WO | WO-2007/123744 A2 | 11/2007 |
| WO | WO-2007/123744 A3 | 11/2007 |

OTHER PUBLICATIONS

International Search Report mailed on Mar. 22, 2022, for PCT Application No. PCT/US2021/063720, filed Dec. 16, 2021, 3 pages.

Pourmand, N. et al. (Apr. 25, 2006, e-published Apr. 13, 2006). "Direct electrical detection of DNA synthesis," *PNAS USA* 103(17): 6466-6470.

Shendure, J. et al. (Sep. 9, 2005, e-published Aug. 4, 2005). "Accurate multiplex polony sequencing of an evolved bacterial genome," *Science* 309(5741):1728-1732.

Written Opinion mailed on Mar. 22, 2022, for PCT Application No. PCT/US2021/063720, filed Dec. 16, 2021, 8 pages.

\* cited by examiner

KINEMATIC IMAGING SYSTEM

CROSS-REFERENCES TO RELATED APPLICATIONS

This application claims the benefit of U.S. Provisional Application No. 63/126,103, filed Dec. 16, 2020, which is incorporated herein by reference in its entirety and for all purposes.

BACKGROUND

A typical bioanalytical instrument (e.g., a nucleic acid sequencing device or system) requires a degree of system magnification to image microscopic features. A potential downside of such magnification is that any magnification present amplifies any tip or tilt distortion of the imaging plane. For example, if the system magnification is 8×, the title at the image plane (i.e., the camera) is 8× the tilt of the sample (e.g., a flow cell or reaction vessel). This undesirably results in optical aberrations and distortions, as well as limits in detection. Disclosed herein, inter alia, are solutions to these and other problems in the art.

BRIEF SUMMARY

Described herein is a bioanalytical instrument, such as a nucleic acid sequencing device or system, that includes at least one camera (e.g., one, two, three, or four cameras) mounted on or otherwise coupled (e.g., attached or affixed) to a kinematic optical mount assembly useful in addressing these and other problems in the art. The kinematic optical mount assembly provides a novel means of camera translocation and rotation relative to an aspect of the bioanalytical instrument, such as relative to a sample coupled to the system, and separates some of the degrees of freedom and permits the camera(s) to capture a greater number of in-focus images as the sample moves. The kinematic optical mount assembly includes one or more electro-mechanical components (e.g., electrically actuated motors) configured to adjust the position and/or orientation of the camera relative to the sample. In addition, the kinematic optical mount assembly is configured to be efficiently attached and detached from the camera for replacement and/or repair.

In one aspect, there is described a kinematic optical mount assembly system, comprising: a base platform; a camera mounted on the base platform; and at least one mechanical component coupled to the base platform, the mechanical component configured to adjust a position or orientation of the camera relative to a sample stage of a nucleic acid sequencing instrument to correct for tilt of an image plane of the camera relative to a sample of the sample stage.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
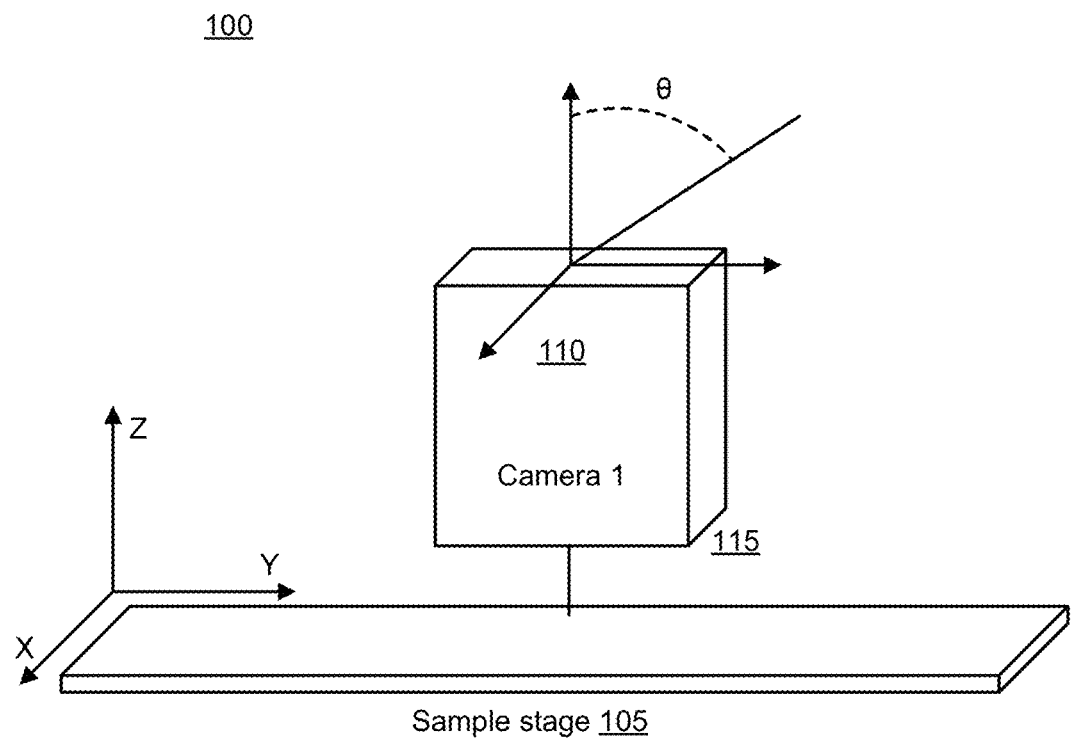
FIG. 1 shows a schematic representation of a kinematic optical mount assembly system, alternatively referred to herein as an imaging system.

FIG. 1 shows a schematic illustration of a bioanalytical instrument 100, which includes a sample stage 105 and a camera 110 positioned relative to the sample stage 105. The camera 110 is removably mounted on or otherwise mechanically coupled to a kinematic optical mount assembly 115, which comprises a kinematic mount. The sample stage is configured to receive or support a sample, for example a sample comprising a flow cell. The sample stage is configured to move along any of x/y/z axes, which are oriented and/or aligned relative to the sample stage 105. To establish a standard coordinate system and frame of reference, it is useful to provide a description of the axes. In conventional descriptions of three-dimensional space using Cartesian coordinates, there are six degrees of freedom. Each degree of freedom corresponds to the translation along and rotations around three perpendicular X-, Y-, and Z-axes. A first degree of freedom can be defined as moving left and right along the X-axis. A second degree of freedom can be defined as moving backward and forward along the Y-axis. A third degree of freedom can be defined as moving up and down along the Z-axis. A fourth degree of freedom can be defined as rotating around the X-axis, or "roll" axis, alternatively referred to as the longitudinal axis. A fifth degree of freedom can be defined as rotating around the Y-axis, or "pitch" axis, alternatively referred to as the transverse axis. Used interchangeably throughout, pitch and roll may be referred to as tip and tilt. A sixth degree of freedom can be defined as rotating around the Z-axis, or "yaw." A plane refers to a 2-dimensional (2D) area defined by two axes (e.g., x and y together form the xy plane). When used in reference to a detecting apparatus and an object observed by the detector, the xy plane may be specified as being orthogonal to the direction of observation between the detector and object being detected. The image plane is a projection of the image on a two-dimensional plane. For example, in embodiments, the image plane is the projection of an image on the surface of the image sensor.

In an aspect is provided an imaging system, including a base platform and a camera including an image sensor, wherein the camera is mounted on the base platform; and at least one mechanical component coupled to the base platform, the mechanical component configured to adjust a position or orientation of the image sensor (e.g., by moving the camera) relative to a sample stage of a bioanalytical instrument to correct for tilt of an image plane of the image sensor relative to a sample of the sample stage. In embodiments, the mechanical component is configured to adjust a position of the image sensor. In embodiments, the mechanical component is configured to adjust an orientation of the image sensor (e.g., adjusting by rotating the camera).

In another aspect is provided an imaging system, including a base platform, a camera mounted on the base platform; and at least one electromechanical component coupled to the base platform, wherein the electromechanical component is configured to adjust a position or orientation of the camera relative to a sample stage of a bioanalytical instrument. In embodiments, adjusting the position or orientation of the camera maximizes the focus (i.e., minimizing the blur circle) of an image. In embodiments, adjusting the position or orientation of the camera corrects for tilt, tip, or both tip and tilt, of an image plane of the image sensor relative to a sample of the sample stage. In embodiments, adjusting the position or orientation of the camera corrects for tilt of an image plane of the image sensor relative to a sample of the sample stage. In embodiments, adjusting the position or orientation of the camera corrects for tip of an image plane of the image sensor relative to a sample of the sample stage. In embodiments, adjusting the position or orientation of the camera corrects for both tip and tilt of an image plane of the image sensor relative to a sample of the sample stage. In embodiments, the position and/or orientation of the camera is adjusted to minimize defocus aberrations. In embodiments, defocus refers to a translation of the focus along the optical axis away from the image sensor. In general, defocus reduces the sharpness and contrast of the image.

In embodiments, adjusting the position or orientation of the camera is automated or semi-automated. As used herein the terms "automated" and "semi-automated" mean that the operations are performed by system programming or configuration with little or no human interaction once the operations are initiated, or once processes including the operations are initiated. For example, the bioanalytic instrument may include a computing device configured to enable adjusting the position or orientation of the camera, including: a processor; memory in electronic communication with the processor; and instructions stored in the memory, the instructions being executable by the processor to adjust the position or orientation of the camera. In embodiments, the position and/or orientation of the camera is adjusted dynamically as the sample is scanned.

In embodiments, the camera includes one or more image sensors, alternatively referred to as a detector. In embodiments, the image sensor is a CMOS array. A CMOS array, alternatively referred to as a CMOS camera, typically use an active-pixel sensor (APS) that is an image sensor comprising of an integrated circuit containing an array of pixels, where each pixel includes a photodetector and an active amplifier. In embodiments, the image sensor includes a PIN photodiode, a CCD array, a CMOS array, a line scanner, a photodiode, a phototransistor, a photomultiplier, or an avalanche photodiode. In embodiments, the image sensor is a CCD array.

In embodiments, the image sensor includes a confocal time delay and integration (TDI) line scan imaging system that has high S/N ratio and high confocality for producing high resolution images of a sample. The image sensor may be or include a complementary metal-oxide-semiconductor (CMOS) array, a charge-coupled device (CCD) array, an array of photodiodes, an array of avalanche photodiodes, an array of photomultiplier tubes (PMTs), or an array of optical fibers. In embodiments, the image sensor is at least one of a complementary metal-oxide-semiconductor (CMOS) array and a charge-coupled device (CCD) array. In embodiments, the image sensor is a complementary metal-oxide-semiconductor (CMOS) array, a charge-coupled device (CCD) array, or a CCD-CMOS sensor array.

In embodiments, the camera further includes one or more lenses, a beam splitter, one or more pinhole apertures, excitation filter, or combinations thereof. In embodiments, the imaging system may also include other components, including a collection of lenses (such as a collimating lens, a beam shaping lens (e.g., Powell lens), and a cylindrical lens), mirrors (e.g., a dichromatic mirror), beam splitter, one or more pinhole apertures, excitation filter, or combinations thereof. For example, the direction, size, and/or polarization of the light source may be adjusted by using lenses, mirrors, and/or polarizers. In embodiments, one or more of the components of the system may be adjusted or manipulated automatically. In embodiments, the imaging system includes one or more optical components (e.g., a beam shaping lens) configured to shape the light emitted from the one or more light sources into desired patterns. For example, in some embodiments, the imaging system further includes one or more optical components that may shape the light into line patterns (e.g., by using one or more Powell lenses, or other beam shaping lenses, diffractive, or scattering components). In embodiments, the imaging system includes a line generator. Exemplary line generators include, but are not limited to, a one dimensional diffuser having angular uniformity, cylindrical micro-lens array, diffractive element or aspheric refractive lens such as a Powell lens. In embodiments, the optical components include a Powell lens, a micro-lens, or micro-lens array. In embodiments, the optical component includes a micro-lens fabricated on glass, metal, or plastic. In embodiments, the excitation beams may be directed through a beam shaping lens or lenses. In some embodiments, a single beam shaping lens may be used to shape the excitation beams output from a plurality light sources (e.g., 2 light sources). In some embodiments, a separate beam shaping lens may be used for each light beam. In embodiments, the beam shaping lens is a Powell lens, alternatively referred to as a Powell prism. The shape of the beam may be shaped into an appropriate geometry according to known techniques, e.g., a line, conical, super-Gaussian, ring, doughnut, Bessel-Gauss, Hermite-Gaussian, Laguerre-Gaussian, Hypergeometric-Gaussian, Ince-Gaussian, and the like. In embodiments, the beam is uniform within acceptable limits (e.g., less than 30% intensity variation across the beam). In embodiments, the beam is profiled or includes a gradient.

The kinematic optical mount assembly 115, alternatively referred to herein as an imaging system, can include a support structure such as a base platform or table that provides at least one surface upon which the camera 110 is removably mounted or attached. In embodiments, the base platform is movable (e.g., capable of rotating) relative to the sample stage. In embodiments, the base platform is stainless steel or black anodized aluminum.

In embodiments, the imaging system includes one camera. In embodiments, the imaging system includes two cameras. In embodiments, the imaging system includes three cameras. In embodiments, the imaging system includes four cameras. In embodiments, the camera is an area scan camera (e.g., the camera contains a matrix or array of pixels that detects an image). In embodiments, the camera is a line scan camera (e.g., the camera contains a row of pixels that detects the image).

In embodiments, the sample stage is capable of moving independently relative to the sample stage base platform. For example, the sample stage may translate (e.g., 0.5 mm to 100 mm) in the xy plane while the camera rotates about a longitudinal and/or transverse axis. In embodiments, the sample stage may translate in the xy plane while the camera remains static. In embodiments, the base platform is capable of rotating relative to the xy plane of the sample on the sample stage. In embodiments, the sample stage is capable of translating in an xy plane, and the image sensor is capable of moving along a polar angle formed between the z axis and the normal vector of the xy plane. In embodiments, the sample stage is capable of translating only in an xy plane, and the image sensor is capable of moving along a polar angle formed between the z axis and the normal vector of the xy plane. In embodiments, the sample stage is mobile (e.g., capable of at least moving in the xy plane). In embodiments, the sample stage is a motorized translation stage. In embodiments, the sample stage is configured to receive and retain a multiwell container or a reaction vessel. In embodiments, the sample stage is configured to receive and retain a reaction vessel containing a sample. In embodiments, the device further includes one or more "fascia plates", or covers, that hides fasteners, circuit boards, and similar delicate components, protecting them from dust and/or human contact, and providing visual appeal. In embodiments, the sample stage is not configured to adjust a position or orientation relative to the camera (e.g., the image sensor of the camera) of a bioanalytical instrument to correct for tilt of an image plane of the image sensor relative to a sample of the sample stage. In embodiments, the sample stage is not configured to rotate about the longitudinal axis. In embodiments, the sample stage is not configured to rotate about the transverse axis. In embodiments, the sample stage is not configured to tip or tilt (e.g., tip or tilt relative to the xy plane). In embodiments, the sample stage is not configured to tilt (e.g., tilt relative to the xy plane).

In embodiments, the xy plane is dynamically determined as the sample is scanned (e.g., continuously scanned in a scan axis, such as the x axis). The system may further include a scanning element, which may be a mechanical, electro-mechanical component, software component, or combination thereof configured to scan the sample along a direction, which may correspond to a scan direction. In an embodiment, the scan direction is orthogonal to the excitation direction of the sample. In an embodiment, the scan direction is non-orthogonal to the excitation beam direction, wherein the orthogonal projected component directly contributes to the final image reconstruction. The term "scanning element" is intended to mean an element capable of sequentially detecting different portions of a sample. A scanning element can operate, by changing the position of one or more component of the system including, for example, the light source the objective lens, the image sensor, or the sample. Exemplary scanning elements include, but are not limited to a galvanometer configured to move a beam (e.g., excitation beam) across a sample or a translation stage configured to move the sample across the beam. In embodiments, the sample is scanned at about 1 mm$^2$/sec, 1.5 mm$^2$/sec, 5 mm$^2$/sec, 10 mm$^2$/sec, 50 mm$^2$/sec or 100 mm$^2$/sec. In embodiments, the sample is scanned at 10 mm$^2$/sec, 20 mm$^2$/sec, 30 mm$^2$/sec, 40 mm$^2$/sec, or 50 mm$^2$/sec. In embodiments, the sample is scanned at least 20 mm$^2$/sec.

The kinematic mount assembly 115 includes one or more mechanical and/or electro-mechanical components that are configured to adjust or move the position or orientation of the camera 110 relative to the sample stage 105. In this regard, the camera 110 can be movably adjusted relative to the kinematic mount assembly 115 and/or the entire kinematic optical mount assembly 115 (including the camera and the kinematic mount) can be movably adjusted relative to the sample stage 105. In embodiments, the electromechanical component moves the camera upward or downward to allow for adjusting the image sensor to an optimal focal plane. In embodiments, the electromechanical component moves the lens of the camera upward or downward. In embodiments, the electromechanical component rotates (e.g., rotates about a longitudinal and/or transverse axis) the camera to allow for adjusting the image sensor to an optimal focal plane.

In embodiments, the at least one electromechanical component includes at least one motor attached (connected) to the base platform. In embodiments, the electromechanical component includes at least one electrically actuated motor attached to the base platform. In embodiments, the electromechanical component includes one, two, three, or four electrically actuated motor(s) attached to the base platform. In embodiments, the electromechanical component includes one electrically actuated motor attached to the base platform. In embodiments, the electromechanical component includes two electrically actuated motors attached to the base platform. In embodiments, the electromechanical component includes at least one linear actuator. In embodiments, the motor is a stepper motor, piezo motor, brushless motor, hysteresis motor, linear motor, or a servomotor. In embodiments, the motor is a stepper motor. In embodiments, the stepper motor includes an integrated ball spline. In embodiments, the motor is a piezo motor. In embodiments, the motor is a brushless motor. In embodiments, the motor is a hysteresis motor. In embodiments, the motor is a linear motor. In embodiments, the motor is a servomotor. In embodiments, the servomotor includes a braking mechanism.

The kinematic optical mount assembly 115 is configured to move in the x, y, and z directions, as well as along its polar angle, θ relative to the sample stage. The polar angle is the angle formed between the z axis and the normal vector of the xy plane. In embodiments, the kinematic optical mount assembly 115 is configured to move along the transverse axis (i.e., the pitch axis) relative to the sample stage. In embodiments, the kinematic optical mount assembly 115 is configured to move along the longitudinal axis (i.e., the roll axis) relative to the sample stage.

In embodiments, the imaging system includes one or more electromechanical components that include a camera-focus-and-tilt motor configured to positionally adjust the camera so that the camera can focus on imaging a region of interest.

The kinematic optical mount assembly 115 is configured to correct or otherwise adjust for tilt of the sample (e.g., a flow cell or reaction vessel) relative to the camera. In this regard, the kinematic optical mount assembly 115 can include one or more mechanical features that are configured to adjust the position and/or orientation of the camera 110 relative to the sample stage 105 such as to translate and/or tilt the kinematic optical mount assembly 115. In embodiments, the imaging system includes defines a tip/tilt plane that is coincident with an image plane of the camera.

For example, the kinematic optical mount assembly 115 can be motorized in a manner that allows for rapid tip and tilt adjustment of the kinematic optical mount assembly 115 and the camera. In a non-limiting example, the kinematic optical mount assembly 115 can include a quantity (such as a quantity of one, two, three, or four) stepper motors configured to positionally adjust the kinematic optical mount assembly 115. The stepper motors can be mechanically coupled to the base platform upon which the camera 110 is mounted so as to positionally adjust the base platform and camera 110. The stepper motor can include an integrated ball spline in a non-limiting example.

The positional adjustment of the camera 110, such as X/Y/θ adjustment of the camera 110, within the kinematic optical mount assembly 115 allows centering of the image sensor (i.e., the camera) with respect to the optical axis and rotational alignment of the image sensor to patterned features in the flow cell and/or the laser illumination area. This has the benefit of trimming out gross optical misalignment. The kinematic optical mount assembly 115 can include camera focus and tilt motors configured to adjust the camera so it may focus on imaging the region of interest as the flow cell moves along a scan direction.

The kinematic optical mount assembly 115 can also comprise one or more locating pins on the base platform to ensure or increase a likelihood of proper location tolerance of the entire assembly with respect to the rest of the microscope assembly.

Figure 2A:
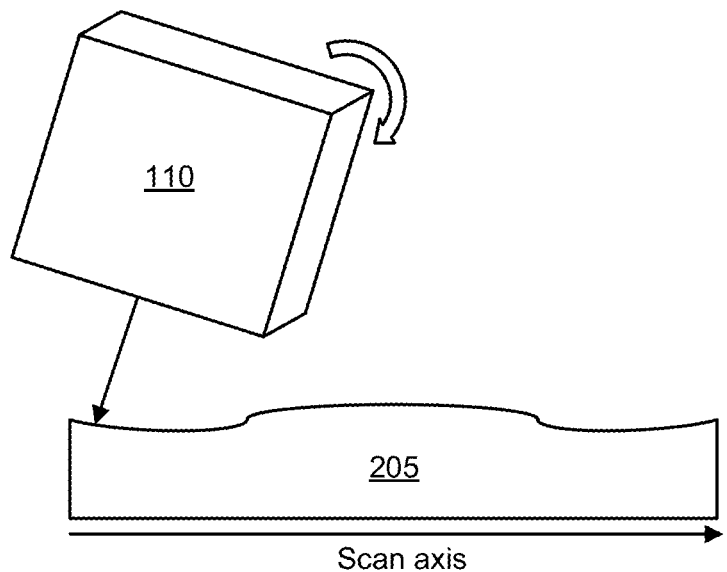
FIGS. 2A-2C schematically shows a camera of the imaging system scanning a sample 205 along a scan axis. The camera 110 includes an image sensor that is capable of rotating about a longitudinal and/or transverse axis in a first example manner or second example manner (e.g., clockwise rotation about a predetermined axis (FIG. 2A) or counter-clockwise rotation about a predetermined axis (FIG. 2C).) In embodiments, the sample 205 does not rotate about the same axes (i.e., the longitudinal and/or transverse axes). The ability to rotate the image sensor about different axes relative to the sample allows the camera to maximize the focus (i.e., maximize convergence of collected light rays). The figures depict adjusting the orientation about one axis, however it is understood that the image sensor is further capable of adjusting about the orthogonal axis.
Figure 2B:
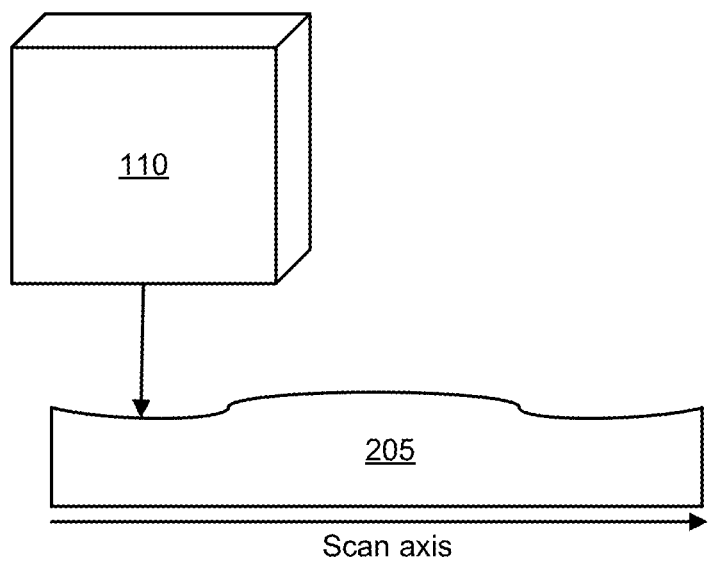
Figure 2C:
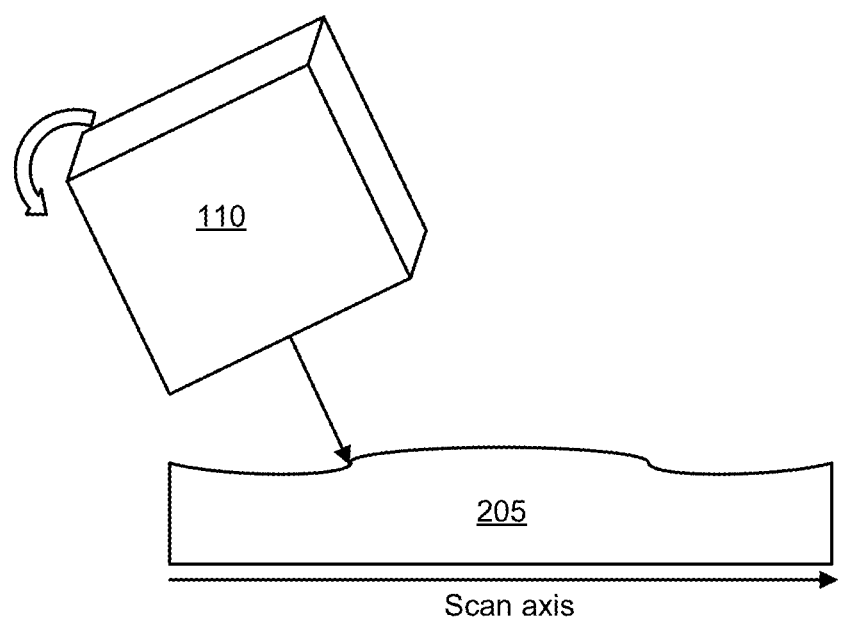

FIGS. 2A-2C schematically illustrate a camera 110 scanning a sample 205 along a scan axis, such as the x axis. The sample 205 (e.g., a flow cell or suitable reaction vessel) may have one or more deformations such that the objective may not be in focus relative to certain portions of the sample as the camera 110 scans the sample 205 along the scan axis. The kinematic optical mount assembly 115 is configured to adjust the position of the camera and/or the orientation of the camera, such as to tilt (e.g., rotate about an axis to adjust an orientation of the camera) the camera to compensate for the deformations. The manner of tilt can vary and can include a roll-type tilt and/or a pitch-type tilt. The positional and/or rotational adjustment is configured to minimize or eliminate any second order aberrations in the image. The solutions provided herein do not require tipping or tilting the sample 205 or sample stage. The system may include two or more sensors parallel to one another within a single camera so it may be useful to adjust pitch to compensate for chromatic focal shift although adjustment of roll may be a primary adjustment or an adjustment in combination with pitch.

In a non-limiting example, the motors (or other mechanical or electromechanical feature) of the kinematic optical mount assembly 115 adjust the camera in less than 0.25 mrad increments, capable of moving a total of +/−10 mrad in total. In embodiments, the motors (or other mechanical or electromechanical feature) of the kinematic optical mount assembly 115 adjust the camera in 0.5, 1.0, 1.5, 2.0, 2.5, 3.0, 3.5, 4.0, 4.5, or 5.0 mrad increments, capable of moving a total of +/−50 mrad in total. In embodiments, the image sensor is capable of moving +/−10 mrad in total, +/−20 mrad in total, +/−30 mrad in total, +/−40 mrad in total, or +/−50 mrad in total.

In embodiments, the kinematic optical mount assembly 115 is further configured to move the motors up or down (i.e. along a Z-axis) to allow for adjusting the camera sensor to the optimal focal plane (Z-position adjustment) to account for lens focal length tolerances, minimizing optical aberrations. In another non-limiting example, the kinematic mount motors adjust the camera in less than 25 μm increments and are capable of adjusting the camera about +/−8 mm to optimize the image in focus. In another non-limiting example, the kinematic mount motors adjust the camera in about 10, 15, 20, 25, 30, 35, 40, 45, or 50 μm increments and are capable of adjusting the camera about +/−200 mm to optimize the image in focus.

The kinematic optical mount assembly system 100 is configured to achieve locational stability of the camera and smooth motion of the camera. The camera 115 can be removed and/or serviced and replaced relative to the kinematic optical mount assembly 115 without the need for realignment of the camera.

In embodiments, the sample stage includes, and optionally retains, a reaction vessel, flow cell, or multiwell container. Those skilled in the art will recognize that a flow cell or other support structure may be used with any of a variety of arrays known in the art to achieve similar results. Such arrays may be formed by arranging biological components of samples randomly or in predefined patterns on the surfaces of the support by any known technique. The term "multiwell container" as used herein, refers to a substrate comprising a surface, the surface including a plurality of reaction chambers separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment.

The reaction chambers may be provided as wells (alternatively referred to as reaction chambers), for example a multiwell container may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced biomolecule adhesion (e.g., poly-L-lysine, silanes, carbon nanotubes, polymers, epoxy resins, or gold). In embodiments, the multiwell container is about 5 inches by about 3.33 inches, and includes a plurality of 5 mm diameter wells. In embodiments, the multiwell container is about 5 inches by about 3.33 inches, and includes a plurality of 6 mm diameter wells. In embodiments, the multiwell container is about 5 inches by about 3.33 inches, and includes a plurality of 7 mm diameter wells. In embodiments, the multiwell container is about 5 inches by about 3.33 inches, and includes a plurality of 7.5 mm diameter wells. In embodiments, the multiwell container is 5 inches by 3.33 inches, and includes a plurality of 7.5 mm diameter wells. In embodiments, the multiwell container is about 5 inches by about 3.33 inches, and includes a plurality of 8 mm diameter wells. In embodiments, the multiwell container is a flat glass or plastic tray in which an array of wells are formed, wherein each well can hold between from a few microliters to hundreds of microliters of fluid reagents and samples.

The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a multiwell container are available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the multiwell container includes 24 substantially round flat bottom wells. In embodiments, the multiwell container includes 48 substantially round flat bottom wells. In embodiments, the multiwell container includes 96 substantially round flat bottom wells. In embodiments, the multiwell container includes 384 substantially square flat bottom wells.

The discrete regions (i.e., features, wells) of the multiwell container may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a polymer or copolymer).

Figure 3:
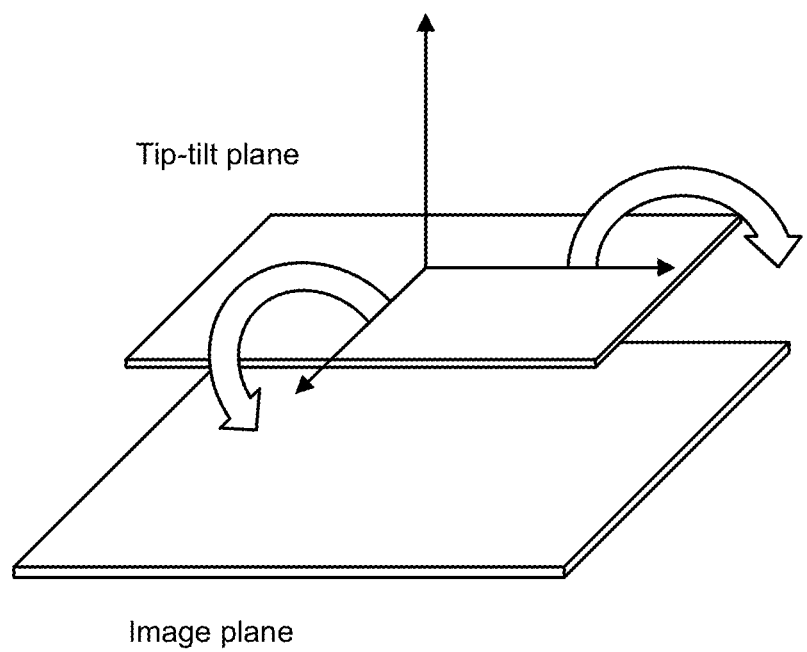
FIG. 3 schematically shows a tip/tilt plane that is coincident with a camera sensor plane (i.e., the image plane). For visualization purposes for this figure, the tip-tilt plane is depicted as being offset from the image plane.

With reference to FIG. 3, the kinematic optical mount assembly 115 further comprises a tip/tilt plane that is coincident with a camera image plane or sensor plane. This can be configured to minimize lateral pixel shift of the sensor (i.e. it is not a true gimbal where the center pixel would not move).

The kinematic optical mount assembly 115 can further comprises means for centering and rotating the camera. This can be in the form of at least one adjustment screw that exerts a force against the base mount upon which the camera is positioned. For example, the at least one adjustment screw can comprise a hardened spherical tip that pushes against a carbide flat rest pad of the kinematic optical mount assembly 115. Adjusting the XY position of the assembly allows for aligning of the center pixel to the true optical axis. The assembly further comprises means for adjusting camera rotation to allow for camera sensor alignment to the laser illumination rectangle (or laser lines/scan direction in the case of TDI imaging). In embodiments, the imaging system further includes an absolute encoder. An absolute encoder provides information about the position (i.e., the distance) the camera, the image sensor, and/or the lens, relative to the sample stage and/or the sample.

Figure 4:
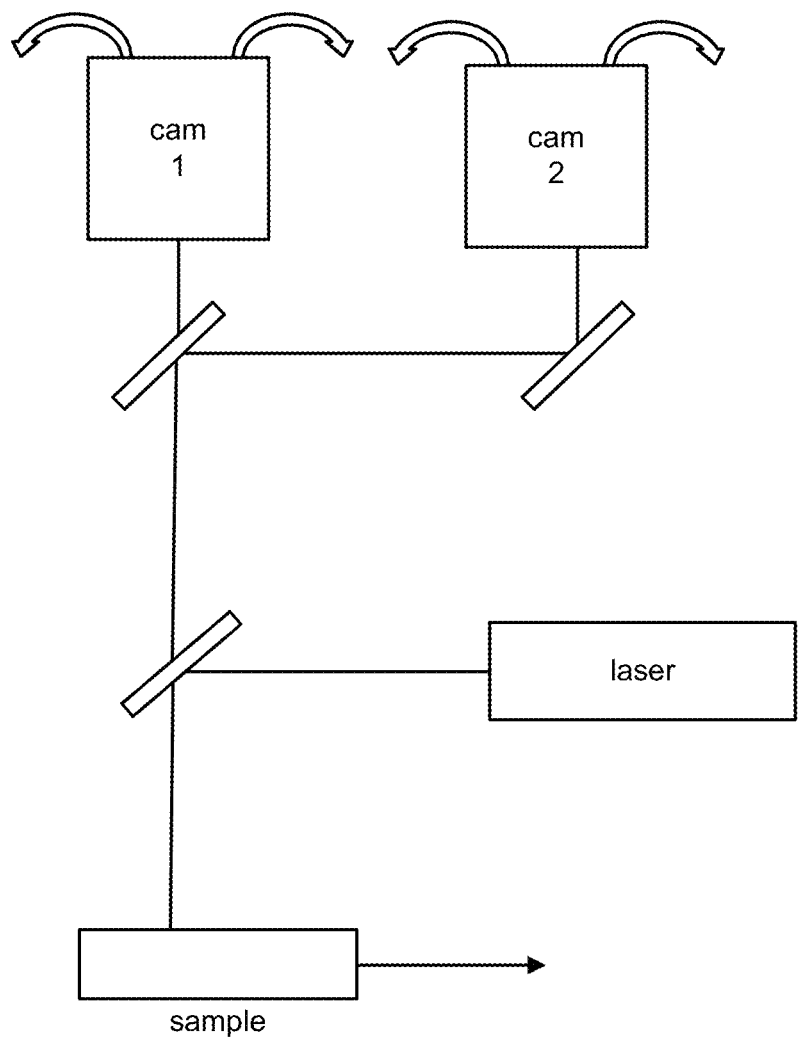
FIG. 4. schematically shows a simplified optics layout showing two cameras. The cameras include arrows depicting the ability to rotate about a single axis (e.g., pitch axis), however it is understood that the cameras are capable of rotating/orienting about a second axis (e.g., the roll axis). The sample is capable of translating (depicted by an arrow) in the xy plane.

FIG. 4 schematically shows a simplified optics layout that includes two cameras, which are referenced as cam 1 and cam 2. Each camera is configured to move independently from each other to increase or maximize the coincidence of the image plane to minimize second order aberrations as the sample moves in the scan dimension. In embodiments, the cameras include an objective lens having high numerical aperture (NA) values. For example, the NA may be at least about 0.65, 0.7, 0.75, 0.8, 0.85, 0.9, 0.95, or higher. Those skilled in the art will appreciate that NA, being dependent upon the index of refraction of the medium in which the lens is working, may be higher including, for example, up to 1.0 for air, 1.33 for pure water, or higher for other media such as oils. However, other embodiments may have lower NA values than the examples listed above. Image data obtained by the optical assembly may have a resolution that is between 0.1 and 50 microns or, more particularly, between 0.1 and 10 microns. In embodiments, the numerical aperture for the camera is at least 0.2. In embodiments, the numerical aperture for the camera is no greater than 0.8. In embodiments, the numerical aperture for the camera is no greater than 0.5. Image systems described herein may have a resolution that is sufficient to individually resolve the features or sites that are separated by a distance of less than 10 µm, 5 µm, 2 µm, 1.5 µm, 1.0 µm, 0.8 µm, 0.5 µm, or less. In embodiments, the image systems described herein may have a resolution that is sufficient to individually resolve the features or sites that are separated by a distance of 100 µm at most.

Depending on the sample, for example the microwells or nanowells of a multiwell container, the imaging system described herein may be configured for wide-field detection. The field diameter for the imaging system may be, for example, at least 0.5 mm, 1 mm, 2 mm, 3 mm, 4 mm, 5 mm or larger. By choosing suitable optical components, the field diameter can be limited to a maximum area as well and, as such the field diameter can be, for example, no larger than 5 mm, 4 mm, 3 mm, 2 mm or 1 mm. For example, in embodiments an image obtained by an imaging system can have an area that is in a range of about 0.25 $mm^2$ to about 25 $mm^2$.

In embodiments, the imaging system may generate image data, for example, at a resolution between 0.1 and 50 microns, which is then forwarded to a control/processing system within the bioanalytical instrument. The control/processing system may perform various operations, such as analog-to-digital conversion, scaling, filtering, and association of the data in multiple frames to appropriately and accurately image multiple sites at specific locations on a sample. The control/processing system may store the image data and may ultimately forward the image data to a post-processing system where the data is further analyzed. For example, further analysis may include determining nucleotide sequence information from the image data. In embodiments, the control/processing system may include hardware, firmware, and software designed to control operation of the bioanalytical instrument. The image data may be analyzed by the bioanalytical instrument itself, or may be stored for analysis by other systems and at different times subsequent to imaging.

In another aspect, there is disclosed a method of imaging a sample. In embodiments, the method includes illuminating a sample and detecting light from the sample (e.g., fluorescent excitation events, scattered light, transmitted light, or reflected light) using the imaging system described herein. In embodiments, the method includes scanning the sample (i.e., translating the sample relative to the camera). In embodiments, the method includes illuminating a sample to generate fluorescent events, and detecting one or more fluorescent events using the imaging system described herein. In embodiments, the method includes detecting clusters (e.g., amplified colonies of nucleic acids) on a solid support. In embodiments, the method includes detecting fluorescently labeled nucleotides incorporated into a template nucleic acid. In embodiments, the method includes sequencing one or more nucleic acid templates.

In embodiments, the sample includes one or more biomolecules. A variety of biomolecules may be present in the sample. Exemplary biomolecules include, without limitation, nucleic acids such as DNA or RNA, proteins such as enzymes or receptors, polypeptides, nucleotides, amino acids, saccharides, cofactors, metabolites or derivatives of these natural components. Although the systems and methods as described herein are with respect to biomolecules, it will be understood that other samples or components can be used as well. For example, synthetic samples can be used such as combinatorial libraries, or libraries of compounds having species known or suspected of having a desired structure or function. In embodiments, the sample includes one or more fluorescent labels. In embodiments, the sample includes one or more fluorescently labeled biomolecules.

In embodiments, one or more line generators (e.g., 2, 4, 6, 8, or 10 lines) are used to illuminate the sample. The one or more line generators may be configured to produce an excitation line having a shape at the sample that is rectangular or oblong. Exemplary shapes include, but are not limited to, a rectangular, elliptical, or oval shape. In embodiments, one or more excitation lines contacts the sample to illuminate and/or excite one or more biomolecules in the sample.

In embodiments, the imaging system is within a bioanalytical instrument. In embodiments, the bioanalytical instrument further includes a light source and an integrated fluidic system of one or more interconnected chambers, ports, and channels in fluid communication and configured for carrying out an analytical reaction or processes.

In an aspect is provided a microfluidic device, wherein the microfluidic device includes an imaging system as described herein. In embodiments, the microfluidic device include one or more reaction vessels or solid support where reagents interact and are imaged. Exemplary systems having fluidic components that can be readily modified for use in a system herein include, but are not limited to, those set forth in U.S. Pat. Nos. 8,241,573, 8,039,817; or US Pat. App. Pub. No. 2012/0270305 A1, each of which is incorporated herein by reference. In embodiments, the microfluidic device further includes one or more excitation lasers.

In embodiments, the device as described herein detects scattered light from the sample.

In embodiments, the device as described herein detects diffracted light from the sample. In embodiments, the device as described herein detects reflected light from the sample. In embodiments, the device as described herein detects absorbed light from the sample. In embodiments, the device as described herein detects refracted light from the sample. In embodiments, the device as described herein detects transmitted light not absorbed by the sample. In embodiments, the device further includes at least one reservoir physically coupled to the structure. In embodiments, the reservoir is configured to store one or more reagents or hold waste material. In some embodiments, the reagents include fluids such as water, buffer solution (e.g., an imaging buffer including ascorbic acid), target capture reagents, or nucleic acid amplification reagents. In some embodiments, the reagent container compartments may be configured to maintain the contents of such containers at prescribed storage temperatures and/or to agitate such containers to maintain the contents of the containers in solution or suspension. In embodiments, the at least one reservoir includes reaction reagents, for example nucleic acid amplification reagents (e.g., polymerase and nucleotides needed for amplification), and/or nucleic acid sequencing reagents. In embodiments, the at least one reservoir includes at least one of a waste reservoir, a sequencing reagent reservoir, a clustering reagent reservoir, and a wash solution reservoir. In embodiments, the device includes a plurality of a sequencing reagent reservoirs and clustering reagent reservoirs. In embodiments, the clustering reagent reservoir includes amplification reagents (e.g., an aqueous buffer containing enzymes, salts, and nucleotides, denaturants, crowding agents, etc.)

In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of the reservoirs can vary. The fluid can be, for example, an aqueous solution which may contain buffers (e.g., saline-sodium citrate (SSC), tris(hydroxymethyl)aminomethane or "Tris"), aqueous salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes.

In embodiments, the microfluidic device includes a computing device. The computing device can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. In embodiments, the computing device includes memory in electronic communication with the processor. The memory architecture may include at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, and data structures that perform particular tasks. The computing device can optionally communicate with one or more external devices such as a keyboard, a pointing device (e.g., a mouse), a display, such as a graphical user interface (GUI), or other device that facilitates focusing an image. Similarly, the computing device can communicate with other devices (e.g., via network card, modem, etc.). Such communication can occur via I/O interfaces. In embodiments, the computing system may communicate with one or more networks such as a local area network (LAN), a general wide area network (WAN), and/or a public network (e.g., the Internet) via a suitable network adapter.

In embodiments, the functions of the image systems described herein may be implemented in hardware, software, firmware, or any combination thereof. If implemented in software, the functions may be stored as one or more instructions or code on a non-transitory computer-readable storage medium or non-transitory processor-readable storage medium. The operations of a method or algorithm disclosed herein may be embodied in a processor-executable software module, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage smart objects, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

In embodiments, the microfluidic device is a nucleic acid sequencing device. Nucleic acid sequencing devices utilize excitation beams to excite labeled nucleotides in the DNA containing sample to enable analysis of the base pairs present within the DNA. Many of the next-generation sequencing (NGS) technologies use a form of sequencing by synthesis (SBS), wherein modified nucleotides are used along with an enzyme to read the sequence of DNA templates in a controlled manner. In embodiments, sequencing includes a sequencing by synthesis event, where individual nucleotides are identified iteratively (e.g., incorporated and detected into a growing complementary strand), as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. In embodiments, the nucleic acid sequencing device utilizes the detection of four different nucleotides that comprise four different labels.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub-combination or a variation of a sub combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "flow cell" refers to the reaction vessel in a microfluidic device (e.g., a nucleic acid sequencing device). The flow cell is typically a glass slide containing small fluidic channels (e.g., a glass slide 75 mm×25 mm×1 mm having one or more channels), through which sequencing solutions (e.g., polymerases, nucleotides, and buffers) may traverse. Though typically glass, suitable flow cell materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, the material of the flow cell is selected due to the ability to conduct thermal energy. In embodiments, a flow cell includes inlet and outlet ports and a flow channel extending therebetween.

A "line generator" as used herein refers to an optical component that is configured to generate a diffraction-limited or near diffraction-limited excitation beam in the plane perpendicular to the optical axis of propagation with a substantially uniform intensity distribution along the horizontal axis of the line. Exemplary line generators include, but are not limited to, a one dimensional diffuser having angular uniformity, cylindrical micro-lens array, diffractive element or aspheric refractive lens such as a Powell lens.

As used herein, the term "substrate" refers to a solid support material. The substrate can be non-porous or porous. The substrate can be rigid or flexible. A nonporous substrate generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located within a flow cell. The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like. The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular.

As used herein, the terms "sequencing", "sequence determination", "determining a nucleotide sequence", and the like include determination of a partial or complete sequence information (e.g., a sequence) of a polynucleotide being sequenced, and particularly physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate within a flow cell (i.e., within a channel of the flow cell). In an embodiment, the sequencing is sequencing by synthesis (SBS). Briefly, SBS methods involve contacting target nucleic acids with one or more labeled nucleotides (e.g., fluorescently labeled) in the presence of a DNA polymerase. Optionally, the labeled nucleotides can further include a reversible termination property that terminates extension once the nucleotide has been incorporated. Thus, for embodiments that use reversible termination, a cleaving solution can be delivered to the flow cell (before or after detection occurs). Washes can be carried out between the various delivery steps. The cycle can then be repeated n times to extend the primer by n nucleotides, thereby detecting a sequence of length n. Exemplary SBS procedures and detection platforms that can be readily adapted for use with the methods of the present disclosure are described, for example, in Bentley et al., Nature 456:53-59 (2008), WO 2004/018497; and WO 2007/123744, each of which is incorporated herein by reference in its entirety. In an embodiment, sequencing is pH-based DNA sequencing. The concept of pH-based DNA sequencing, has been described in the literature, including the following references that are incorporated by reference: US2009/0026082; and Pourmand et al, Proc. Natl. Acad. Sci., 103: 6466-6470 (2006) which are incorporated herein by reference in their entirety. Other sequencing procedures that use cyclic reactions can be used, such as pyrosequencing. Sequencing-by-ligation reactions are also useful including, for example, those described in Shendure et al. Science 309:1728-1732 (2005).

As used herein, the term "feature" refers a point or area in a pattern that can be distinguished from other points or areas according to its relative location. An individual feature can include one or more polynucleotides. For example, a feature can include a single target nucleic acid molecule having a particular sequence or a feature can include several nucleic acid molecules having the same sequence (and/or complementary sequence, thereof). Different molecules that are at different features of a pattern can be differentiated from each other according to the locations of the features in the pattern. Non-limiting examples of features include wells in a substrate, particles (e.g., beads) in or on a substrate, polymers in or on a substrate, projections from a substrate, ridges on a substrate, or channels in a substrate.

The term "image" is used according to its ordinary meaning and refers to a representation of all or part of an object. The representation may be an optically detected reproduction. For example, an image can be obtained from fluorescent, luminescent, scatter, or absorption signals. The part of the object that is present in an image can be the surface or other xy plane of the object. Typically, an image is a 2-dimensional representation of a 3 dimensional object. An image may include signals at differing intensities (i.e., signal levels). An image can be provided in a computer readable format or medium. An image is derived from the collection of focus points of light rays coming from an object (e.g., the sample), which may be detected by any image sensor.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2 dimensional area defined by straight line axes x and y. When used in reference to a detecting apparatus and an object observed by the detector, the xy plane may be specified as being orthogonal to the direction of observation between the detector and object being detected.

As used herein, the term "label" or "labels" generally refer to molecules that can directly or indirectly produce or result in a detectable signal either by themselves or upon interaction with another molecule. A label moiety can be any moiety that allows the sample to be detected, for example, using a spectroscopic method. Exemplary label moieties are fluorescent labels, mass labels, chemiluminescent labels, electrochemical labels, detectable labels and the like. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, the label is a fluorophore. Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye).

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The term "optical filter" refers to a device for selectively passing or rejecting passage of radiation in a wavelength, polarization, or frequency dependent manner. In embodiments, an optical filter is a dichroic filter or dielectric filter. The fluorescence from different fluorophores could be further separated by dichromatic optical elements and projected into spatially separated lines on the sensor array. To further suppress the background from out-of-the-focus fluorescence signal, an optical filter with multiple stripe patterns may be placed in front of the camera to pass only the selected fluorescence lines and reject the unwanted ones. An optical filter is used in accordance with its plain ordinary meaning in the art and refers to a device for selectively passing or rejecting the passage of light having a particular wavelength, polarization or frequency. The term can include an interference filter in which multiple layers of dielectric materials pass or reflect light according to constructive or destructive interference between reflections from the various layers. Interference filters are also referred to in the art as dichroic filters, or dielectric filters. The term can include an absorptive filter which prevents the passage of light having a selective wavelength or wavelength range by absorption. Absorptive filters include, for example, colored glass or liquid. A filter can have one or more particular filter transmission characteristics including, for example, bandpass, short pass and long pass. A band pass filter selectively passes light in a wavelength range defined by a center wavelength of maximum radiation transmission ($T_{max}$) and a bandwidth and blocks passage of light outside of this range. $T_{max}$ defines the percentage of radiation transmitted at the center wavelength. The bandwidth is typically described as the full width at half maximum (FWHM) which is the range of wavelengths passed by the filter at a transmission value that is half of $T_{max}$. A band pass filter can have a FWHM of 10 nanometers (nm), 20 nm, 30 nm, 40 nm or 50 nm. A long pass filter selectively passes higher wavelength light as defined by a $T_{max}$ and a cut on wavelength. The cut on wavelength is the wavelength at which light transmission is half of $T_{max}$, when the wavelength increases above the cut on wavelength, transmission percentage increases and as wavelength decreases below the cut on wavelength transmission percentage decreases. A short pass filter selectively passes lower wavelength radiation as defined by a $T_{max}$ and a cut off wavelength. The cut off wavelength is the wavelength at which light transmission is half of $T_{max}$; as wavelength increases above the cut off wavelength, transmission percentage decreases and as wavelength decreases below the cut off wavelength transmission percentage increases. A filter can have a $T_{max}$ of 50-100%, 60-90% or 70-80%.

The term "nucleic acid sequencing device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems (e.g., one or more lasers and one or more optical sensors such as a camera, objective, and lenses for detecting fluorescence), data collection and/or integration systems, for the purpose of determining the nucleic acid sequence of a template polynucleotide. Nucleic acid sequencing devices may further include valves, pumps, and specialized functional coatings on interior walls. Nucleic acid sequencing devices may include a receiving unit, or platen, that orients the flow cell such that a maximal surface area of the flow cell is available to be exposed to an optical lens. Other nucleic acid sequencing devices include those provided by Illumina™, Inc. (e.g. HiSeg™, MiSeq™, NextSeg™, or NovaSeg™ systems), Life Technologies™ (e.g. ABI PRISM™, or SOLiD™ systems), Pacific Biosciences (e.g. systems using SMRT™ Technology such as the Sequel™ or RS II™ systems), or Qiagen (e.g. Genereader™ system). Nucleic acid sequencing devices may further include fluidic reservoirs (e.g., bottles), valves, pressure sources, pumps, sensors, control systems, valves, pumps, and specialized functional coatings on interior walls. In embodiments, the device includes a plurality of a sequencing reagent reservoirs and a plurality of clustering reagent reservoirs. In embodiments, the clustering reagent reservoir includes amplification reagents (e.g., an aqueous buffer containing enzymes, salts, and nucleotides, denaturants, crowding agents, etc.) In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of each of the reservoirs can vary. The fluid can be, for example, an aqueous solution which may contain buffers (e.g., saline-sodium citrate (SSC), ascorbic acid, tris(hydroxymethyl)aminomethane or "Tris"), aqueous salts (e.g., KCl or (NH4)2SO4)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes. In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED).

In embodiments, the nucleic acid sequencing device includes an imaging system (e.g., an imaging system as described herein). The imaging system capable of exciting one or more of the identifiable labels (e.g., a fluorescent label) linked to a nucleotide and thereafter obtain image data for the identifiable labels. The image data (e.g., detection data) may be analyzed by another component within the device. The imaging system may include a system described herein and may include a fluorescence spectrophotometer including an objective lens and/or a solid-state imaging device. The solid-state imaging device may include a charge coupled device (CCD) and/or a complementary metal oxide semiconductor (CMOS).

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. A clow cell may include an array and can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/cm$^2$, at least about 1,000 features/cm$^2$, at least about 10,000 features/cm$^2$, at least about 100,000 features/cm$^2$, at least about 10,000,000 features/cm$^2$, at least about 100,000,000 features/cm$^2$, at least about 1,000,000,000 features/cm$^2$, at least about 2,000,000,000 features/cm$^2$ or higher. In embodiments, the arrays have features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher. Clustering refers to the process of generating clusters (i.e., solid-phase amplification of polynucleotides).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

Embodiment P1. A kinematic optical mount assembly system, comprising: a base platform; a camera mounted on the base platform; at least one mechanical component coupled to the base platform, the mechanical component configured to adjust a position or orientation of the camera relative to a sample stage of a nucleic acid sequencing instrument to correct for tilt of an image plane of the camera relative to a sample of the sample stage.

Embodiment P2. The kinematic optical mount assembly system of Embodiment P1, wherein the at least one mechanical component comprises at least one motor attached to the base platform.

Embodiment P3. The kinematic optical mount assembly system of Embodiment P2, wherein the at least one motor is a stepper motor.

Embodiment P4. The kinematic optical mount assembly system of Embodiment P3, wherein the stepper motor includes an integrated ball spline.

Embodiment P5. The kinematic optical mount assembly system of Embodiment P1, wherein the at least one mechanical component comprises at least one camera focus and tilt motor configured to positionally adjust the camera so that the camera can focus on imaging a region of interest.

Embodiment P6. The kinematic optical mount assembly system of Embodiment P1, wherein the system defines a tip/tilt plane that is coincident with an image plane of the camera.

Embodiment P7. The kinematic optical mount assembly system of Embodiment P1, wherein the base platform is movable relative to the sample stage.

Embodiment P8. The kinematic optical mount assembly system of Embodiment P1, wherein the at least one mechanical component adjusts a position or orientation of the camera relative to a sample stage as a flow cell of the sample stage moves along a scan direction.

Embodiment P9. The kinematic optical mount assembly system of Embodiment P1, wherein the at least one mechanical component moves the camera upward or downward to allow for adjusting a camera sensor to an optimal focal plane.

Embodiment P10. The kinematic optical mount assembly system of Embodiment P1, wherein the at least one mechanical component is configured to rotate the camera.

Embodiment P11. The kinematic optical mount assembly system of Embodiment P1, further comprising a flow cell.

Embodiment P12. The kinematic optical mount assembly system of Embodiment P1, wherein the kinematic optical mount assembly system is part of a bioanalytical instrument.

What is claimed is:
1. An imaging system, comprising:
a base platform;
a camera mounted on the base platform;
at least one electromechanical component coupled to the base platform, the electromechanical component con- figured to adjust a position or orientation of the camera relative to a sample stage of a bioanalytical instrument to correct for tilt of an image plane of the camera relative to a sample of the sample stage;

wherein the sample stage translates in an xy plane, and the at least one electromechanical component automatically moves the camera along a polar angle formed between the z axis and the normal vector of the xy plane.

2. The imaging system of claim 1, wherein the camera comprises a complementary metal-oxide-semiconductor (CMOS) array, a charge-coupled device (CCD) array, or a CCD-CMOS sensor array.

3. The imaging system of claim 1, wherein the at least one electromechanical component comprises at least one motor attached to the base platform.

4. The imaging system of claim 3, wherein the at least one motor is a stepper motor, piezo motor, brushless motor, hysteresis motor, linear motor, or a servomotor.

5. The imaging system of claim 4, wherein the stepper motor includes an integrated ball spline.

6. The imaging system of claim 1, wherein the at least one electromechanical component comprises at least one electrically actuated motor attached to the base platform.

7. The imaging system of claim 1, wherein the at least one electromechanical component comprises at least one camera focus and tilt motor configured to positionally adjust the camera so that the camera can focus on imaging a region of interest.

8. The imaging system of claim 1, wherein the imaging system defines a tip/tilt plane that is coincident with an image plane of the camera.

9. The imaging system of claim 1, wherein the base platform is movable relative to the sample stage.

10. The imaging system of claim 1, wherein the sample stage is capable of moving independently relative to the sample stage base platform.

11. The imaging system of claim 1, wherein the at least one electromechanical component automatically moves the camera upward or downward to allow for adjusting the camera to an optimal focal plane.

12. The imaging system of claim 1, wherein the at least one electromechanical component is configured to rotate the camera.

13. The imaging system of claim 1, wherein the at least one electromechanical component rotates the camera to allow for adjusting the camera to an optimal focal plane.

14. The imaging system of claim 1, wherein the sample stage further comprises a flow cell or a multiwell container.

15. The imaging system of claim 1, wherein the camera further comprises one or more lenses, a beam splitter, one or more pinhole apertures, excitation filter, or combinations thereof.

16. The imaging system of claim 15, wherein the at least one mechanical component moves the one or more lenses upward or downward to allow for adjusting the camera to an optimal focal plane.

17. The imaging system of claim 1, wherein the bioanalytical instrument further comprises a light source and an integrated fluidic system of one or more interconnected chambers, ports, and channels in fluid communication and configured for carrying out an analytical reaction or processes.

18. A method of imaging a sample, said method comprising obtaining an image of the sample using the imaging system of claim 1.

19. The method of claim 18, wherein the sample comprises one or more fluorescently labeled biomolecules.

* * * * *